United States Patent [19]

Miyakami et al.

[11] Patent Number: 4,904,289

[45] Date of Patent: Feb. 27, 1990

[54] DEODORIZING APPARATUS

[75] Inventors: Junji Miyakami, Suita; Yuzo Yoshioka, Takatsuki; Kazuhiko Otozi, Yao; Hiroyasu Nakagawa, Kashihara; Toshiyuki Shirouzu; Fumio Yada, both of Yao, all of Japan

[73] Assignee: Sharp Kabushki Kaisha, Osaka, Japan

[21] Appl. No.: 167,320

[22] Filed: Mar. 11, 1988

[30] Foreign Application Priority Data

| Mar. 13, 1987 | [JP] | Japan | 62-37520 |
| Mar. 25, 1987 | [JP] | Japan | 62-44989 |
| Mar. 25, 1987 | [JP] | Japan | 62-44990 |
| Apr. 17, 1987 | [JP] | Japan | 62-59013 |
| Apr. 20, 1987 | [JP] | Japan | 62-60501 |
| Apr. 21, 1987 | [JP] | Japan | 62-60369 |
| Apr. 22, 1987 | [JP] | Japan | 62-60892 |
| Apr. 24, 1987 | [JP] | Japan | 62-62918 |
| Jul. 17, 1987 | [JP] | Japan | 62-110211 |

[51] Int. Cl.$^4$ .............................................. F24F 3/16
[52] U.S. Cl. .......................................... 62/157; 62/78; 204/176
[58] Field of Search .................. 204/176; 62/78, 231, 62/157; 422/4, 306

[56] References Cited

U.S. PATENT DOCUMENTS

| 1,714,562 | 5/1929 | Keiser | 62/78 |
| 1,837,296 | 12/1931 | Speer | 62/78 X |
| 1,961,878 | 6/1934 | Gilkey | 23/4 |
| 2,116,480 | 5/1938 | Smith | 62/78 |
| 2,173,073 | 9/1939 | Pierson | 261/104 |
| 2,203,188 | 6/1940 | Beer | 62/78 |
| 2,212,109 | 8/1940 | Abraham | 62/78 |
| 2,331,147 | 10/1943 | Smith | 99/271 |
| 2,920,622 | 1/1960 | Steel | 128/191 |
| 3,230,033 | 1/1966 | Hamilton et al. | 21/74 |
| 3,421,836 | 1/1969 | Sundin et al. | 21/53 |
| 4,051,045 | 9/1977 | Yamamoto et al. | 204/176 X |
| 4,587,591 | 5/1986 | Adatto et al. | 204/176 X |

Primary Examiner—William E. Wayner
Attorney, Agent, or Firm—Birch, Stewart, Kolasch & Birch

[57] ABSTRACT

A deodorizing apparatus includes a case having an air inlet and an air outlet, an ozone generator of the discharge type disposed in an air flow channel between the air inlet and the air outlet, an acceleration device disposed in the air flow channel at the air outlet side thereof for accelerating the decomposition of odors and ozone, a fan provided within the case, an electric motor provided within the case for driving the fan, and device disposed in the air flow channel at the air inlet side thereof for preventing an excess of ozone from flowing out. As a result, odors can be efficiently removed by a decomposition with ozone, while the leakage of residual ozone is minimized.

30 Claims, 11 Drawing Sheets

The primary voltage of a high voltage generating unit (V)

DEODORIZING APPARATUS

BACKGROUND OF THE INVENTION

1. Field of the Invention

The present invention relates to a deodorizing apparatus for use in storage chambers, such as refrigerators, for removing odors from the air by converting the oxygen in the air to ozone.

2. Description of the Prior Art

Conventionally, active carbon is used, for example, in refrigerators for removing the odors released from the foods stored therein by utilizing the adsorbing property of the carbon. However, active carbon needs replacement every time the active carbon has been saturated by adsorbing odors. Active carbon further has the drawback of requiring replacement at short time intervals since it is difficult to determine when the active carbon has been saturated.

To obviate these drawbacks, deodorizing apparatus have already been proposed in which some of the oxygen in the odor-containing air is converted by a silent discharge to ozone, which is then reacted with the air on the surface of a catalyst for deodorization. With these deodorizing apparatus, the odor components are decomposed on oxidation by the deodorizing catalyst which is activated with ozone at the same time, an excess of the ozone decomposes to oxygen ($2O_3 \rightarrow 3O_2$), and is discharged from the apparatus. (See, for example, Examined Japanese Utility Model Publication SHO 60-24351).

However, the conventional deodorizing apparatus has the drawback that when the operation of the electric motor thereof stops due to a malfunction or due to some other cause, the remaining ozone flows out of the case through an air inlet. As a result, this remaining ozone produces an adverse influence on the interior material of the storage chamber and on the food stored therein.

The apparatus has another drawback. The deodorizing catalyst, when used for a prolonged period of time, exhibits a decreased ozone decomposition efficiency. The amount of residual ozone in the oxygen flowing out of the apparatus increases and a higher residual ozone concentration is produced to the interior of the storage chamber and adversely affect the interior material and the stored food therein.

SUMMARY OF THE INVENTION

The present invention provides a deodorizing apparatus which includes a case having an air inlet and an air outlet, an ozone generator of the discharge type disposed in an air flow channel between the air inlet and the air outlet, an acceleration device disposed in the air flow channel at the air outlet side thereof for accelerating the decomposition of odors and ozone, a fan provided within the case, an electric motor provided within the case for driving the fan, and device disposed in the air flow channel at the air inlet side thereof for preventing an excess of ozone from flowing out.

Preferably, a preventing device is a second device for accelerating the decomposition of odors and ozone. The preventing device may be an electric motor when the motor is disposed in the air flow channel at the air inlet side thereof.

The invention provides a deodorizing apparatus of the type described above which does not allow the residual ozone to flow out of the case of the apparatus even if the operation of the electric fan stops.

Furthermore, the ozone generator is operated intermittently at a specified interval for producing a predetermined amount of ozone in accordance with the capacity and construction of the storage chamber in which the deodorizing apparatus is installed. Additionally, the ozone concentration within the storage chamber may be readily controlled to be less than a given regulation value by utilizing such variations in the interior ozone concentration that increases due to the presence of residual ozone while the generator is in operation but decreases due to the spontaneous decomposition of ozone to oxygen ($2O_3 \rightarrow 3O_2$), leakage, etc. while the generator is out of operation.

The present invention will become more fully understood from the detailed description given hereinbelow and the accompanying drawings which are given by way of illustration only, and thus, are not limitative of the present invention, and wherein:

BRIEF DESCRIPTION OF THE DRAWINGS

FIG. 14 (a) to FIG. 14 (c) are flow charts illustrating the operation of the control circuit of FIG. 8.

DESCRIPTION OF THE PREFERRED EMBODIMENTS

Figure 1:
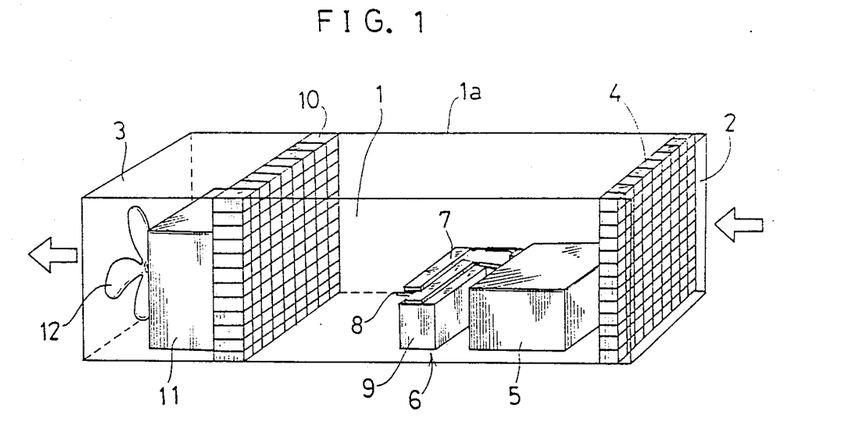
FIG. 1 is a perspective view showing the basic construction of a deodorizing apparatus in a first embodiment of the invention.

FIG. 1 shows the basic construction of a deodorizing apparatus in a first embodiment of the invention.

The apparatus of FIG. 1 has a case 1a for providing an air flow channel 1. The case 1a has at its front and rear ends an air inlet 2 for taking in air containing odors and an air outlet 3. The upstream end of the air flow channel 1 has the inlet 2 positioned for allowing the air to start flowing through the channel and is provided with a deodorizing catalyst 4, which resembles a plate having a honeycomb structure, for accelerating the decomposition of the odors and ozone. A high voltage generating unit 5 is disposed in the channel 1 downstream from the catalyst 4. In the channel downstream from the unit 5, an ozone generator 6 is disposed which includes a high-voltage electrode 7, a low-voltage electrode 8 and an electrode support 9. The air flow channel 1 is further provided with a deodorizing catalyst 10 which is similar to the catalyst 4 and is positioned downstream from the ozone generator 6, a motor 11 and a fan 12 which is attached to the motor 11.

The deodorizing catalysts 4, and 10 have catalytic activity for adsorbing or decomposing odor components and also for decomposing an excess of ozone. More specifically, these catalysts include a composite substrate of titania with silica and manganese oxide coating the substrate surface.

When the deodorizing apparatus of the above construction is driven, the motor 11 rotates the fan 12, so that the odor-containing air is brought into the apparatus through the air inlet 2. On the other hand, a high voltage is supplied from the high voltage generating unit 5 to the ozone generator 6, and a silent discharge is produced across the high-voltage electrode 7 and the low-voltage electrode 8. While the air introduced into the channel 1 is sent toward the air outlet 3 by the fan 12, a portion of the air has its oxygen converted to ozone ($O_3$) by the silent discharge. The air flowing into the case 1a contains odor components and passes through the deodorizing catalyst 10 along with the ozone produced by the generator 6. The catalyst 10, which is activated with the ozone, decomposes the odor components on oxidation. At the same time, an excess of ozone decomposes to oxygen ($2O_3 \rightarrow 3O_2$), and is then sent out from the case 1a through the outlet 3.

If the fan 12 only is out of operation because of a malfunction or some other cause while the ozone generator 6 is in normal operation, the air does not always flow from the inlet 2 toward the outlet 3 (forward flow) but, the air is likely to flow from the outlet 3 toward the inlet 2 (reverse flow). According to the present invention, however, if a reverse flow occurs while ozone is being produced in the apparatus, the ozone within the apparatus is decomposed to oxygen by the deodorizing catalyst 4 before passing through the inlet 2. This eliminates the likelihood of the remaining ozone flowing out from the inlet 2, and the apparatus provides improved safety.

Figure 2:
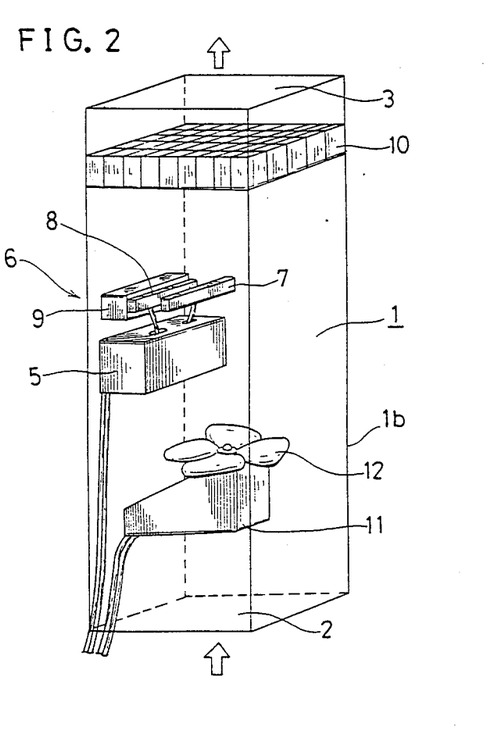
FIG. 2 is a perspective view showing the basic construction of a deodorizing apparatus in a second embodiment of the invention.

FIG. 2 is a perspective view showing the basic construction of a second embodiment of the invention.

The deodorizing apparatus of FIG. 2 has an upright case 1b for providing an air flow channel 1. The case 1b at its lower and upper ends an air inlet 2 for taking in odor-containing air and an air outlet 3, respectively. Between the inlet 2 and the outlet 3, the channel 1 is provided with a motor 11, a fan 12 attached to the motor 11, an ozone generator 6 and, a honeycomb deodorizing catalyst 10 which are arranged downstream from the inlet 2 toward the outlet 3 in the above described order.

When the apparatus is driven, the motor 11 rotates the fan 12, and the odor-containing air is taken into the flow channel 1, while a silent discharge occurs in the ozone generator 6 across a high-voltage electrode 7 and a low-voltage electrode 8 for producing ozone.

The air taken into the channel 1 is sent toward the outlet 3 by the fan. At this time, the odor components in the air come into contact with the deodorizing catalyst 10 which is activated by the ozone. Thereby, the odor components are subjected to accelerated oxidation and are decomposed into odorless components. An excess of ozone is also decomposed to oxygen when passing through the catalyst 10.

While the fan 12 is in normal operation, the ozone from the generator 6 is decomposed by being passed through the catalyst 10 as stated above and therefore the ozone does not flow out. Nevertheless, if the motor stops for one reason or another, the ozone would flow toward the air inlet and flow in a reverse direction out therefrom in the case of the conventional apparatus, whereby, the reverse flow is avoidable in the present deodorizing apparatus of the upright type because the air inlet 2, the motor 11, the ozone generator 6, the deodorizing catalyst 10 and the air outlet 3 are arranged from the lowermost position upward. Even if the motor 11 of the present apparatus becomes locked and stops the fan 12, the heat generated by the locked motor 11 produces an upward air current, so that the ozone produced by the generator 6 is forced upward and is precluded from flowing out via the inlet 2.

Deodorizing apparatus of the basic constructions of FIGS. 1 and 2 are divided generally into unit types which can be removably installed in storage chambers such as refrigerators, and those which are incorporated into storage chambers.

Figure 3:
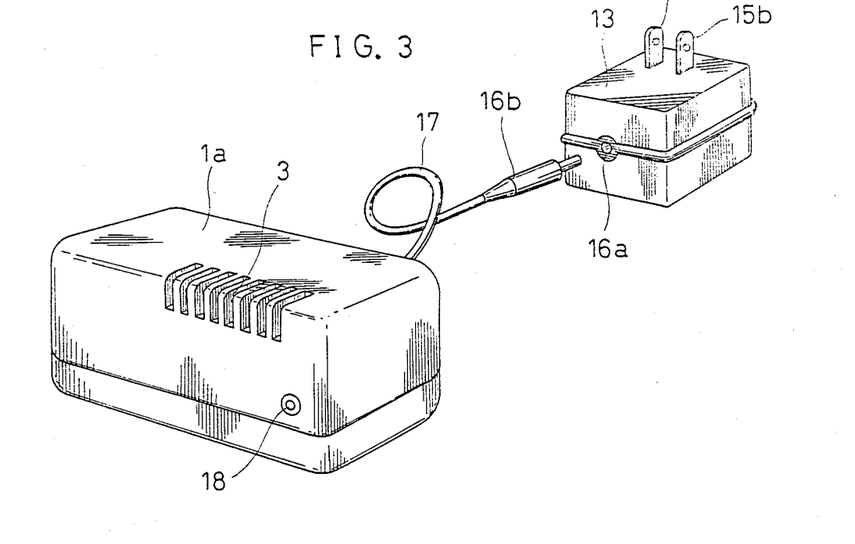
FIG. 3 is a perspective view showing a deodorizing apparatus in the form of a unit and having the basic construction of FIG. 1.
Figure 4:
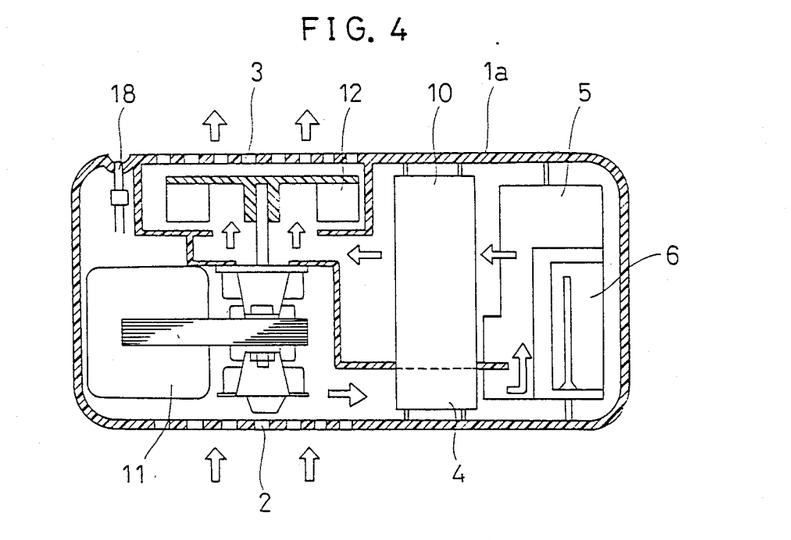
FIG. 4 is a fragmentary sectional view of FIG. 3.
Figure 5:
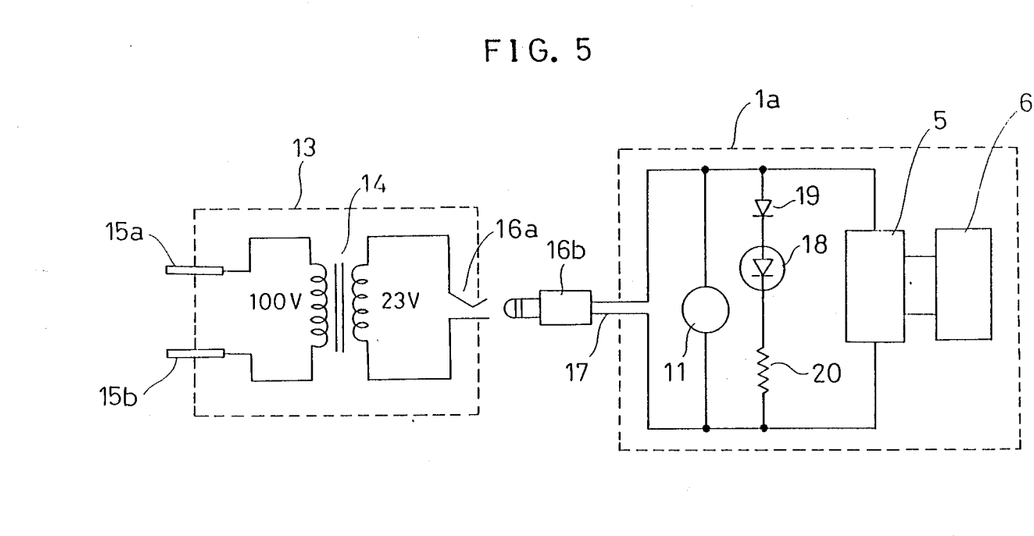
FIG. 5 is a diagram showing the electric circuit of the apparatus of FIG. 3.

FIG. 3 is a perspective view of a deodorizing apparatus of the unit type having the basic construction of FIG. 1, FIG. 4 is a sectional view for the same type, and FIG. 5 is a diagram showing the electric circuit of the apparatus of FIG. 3. These drawings show a transformer case 13 which houses a transformer 14 for stepping down a.c. 100 V to a.c. 23 V, blades 15a and 15b which connect to the primary winding of the transformer 14 for inserting into an a.c. 100 V receptacle, a jack 16a for removably receiving therein a plug 16a, a two-core cable 17 having a plug 16b at one end and fixed to the case 1a at the opposite end, an LED 18, a diode 19 for rectifying the alternating current supplied through the cable 17, and a resistor 20 to setting a current for the LED 18. Throughout FIGS. 1 and FIGS. 3 to 5, like parts are designated by like reference numerals.

When the apparatus is to be used, the case 1a is placed on a shelf within an unillustrated refrigerator having a door, the forward end of the cable 17 is withdrawn from the refrigerator through a clearance between the refrigerator body and its door, and the cable 17 is fixed to the inner wall of the refrigerator with adhesive tape. Additionally, the blades 15a and 15b of the case 13 are inserted into an a.c. 100 V receptacle on an interior wall of the room. The plug 16b at the cable end is inserted into the jack 16a, so that the LED 18 is turned on and the motor 11 and the ozone generator 6 are driven. The odor-containing air within the refrigerator is taken into the case 1a, deodorized and discharged therefrom as indicated by arrows in FIG. 4. The transformer 14 steps down the voltage supplied by the two-core cable 17 and permits the use of the cable 17 having a reduced size which can be drawn out from the refrigerator.

Figure 6:
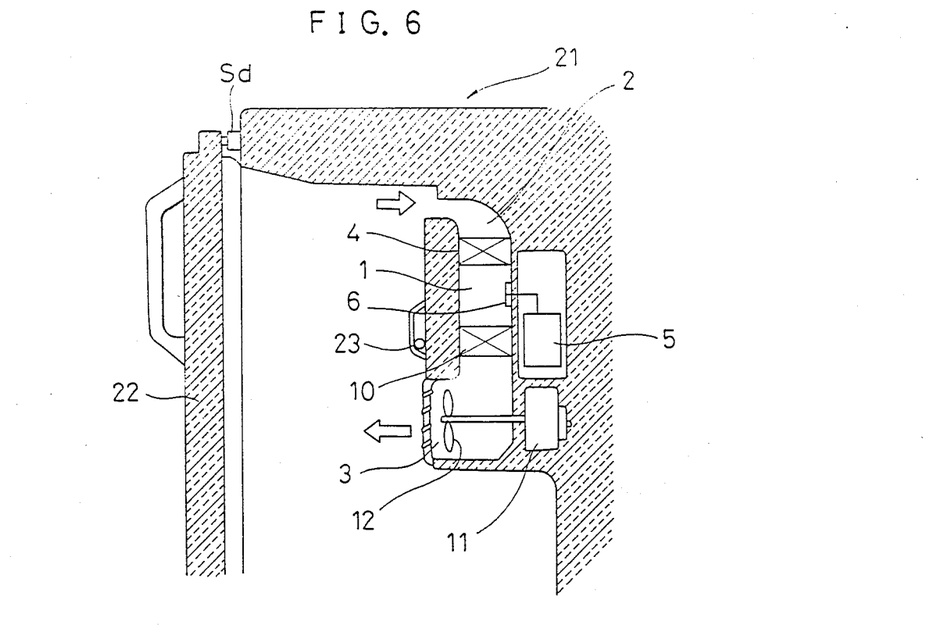
FIG. 6 is a view showing the interior arrangement of a refrigerator having incorporated therein the apparatus of FIG. 1.
Figure 7:
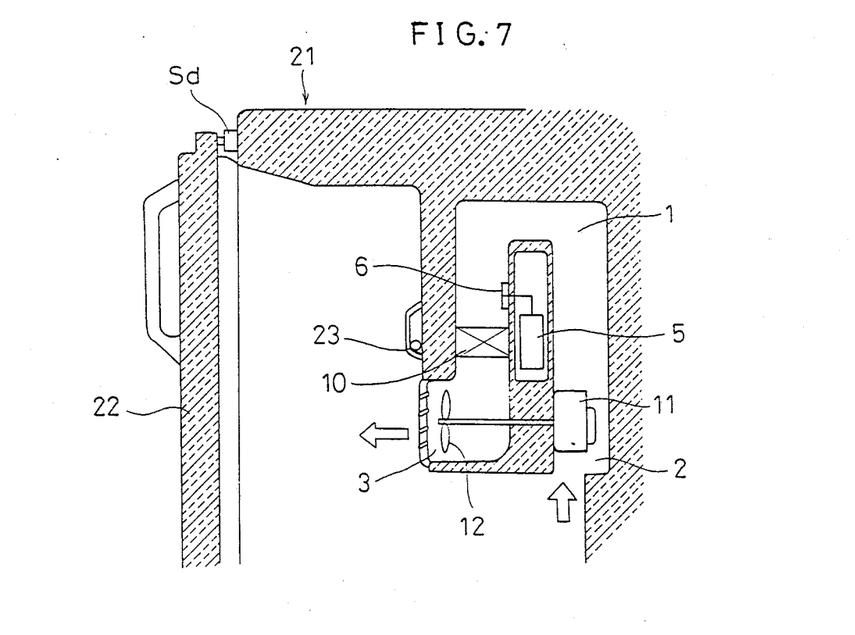
FIG. 7 is a view showing the interior arrangement of a refrigerator having incorporated therein the apparatus of FIG. 2.

FIG. 6 is a view illustrating the interior arrangement of a refrigerator having incorporated therein the apparatus of FIG. 1, and FIG. 7 is a view showing the apparatus of FIG. 2 as similarly incorporated into a refrigerator. With reference to FIGS. 6 and 7, the refrigerator 21 and the door 22, thereof, are indicated. Sd indicates a door switch which is operable with the closing of the door, and a temperature sensor 23 is indicated for detecting the internal temperature of the refrigerator. Throughout FIGS. 1, 2, 6 and 7, like parts are designated by like reference numerals or symbols. With reference to FIG. 7, the air flow channel 1 is U-shaped, and the fan 12, which is disposed at the air outlet 3, is driven by the motor 11 which is positioned at the air inlet 2.

Figure 8:
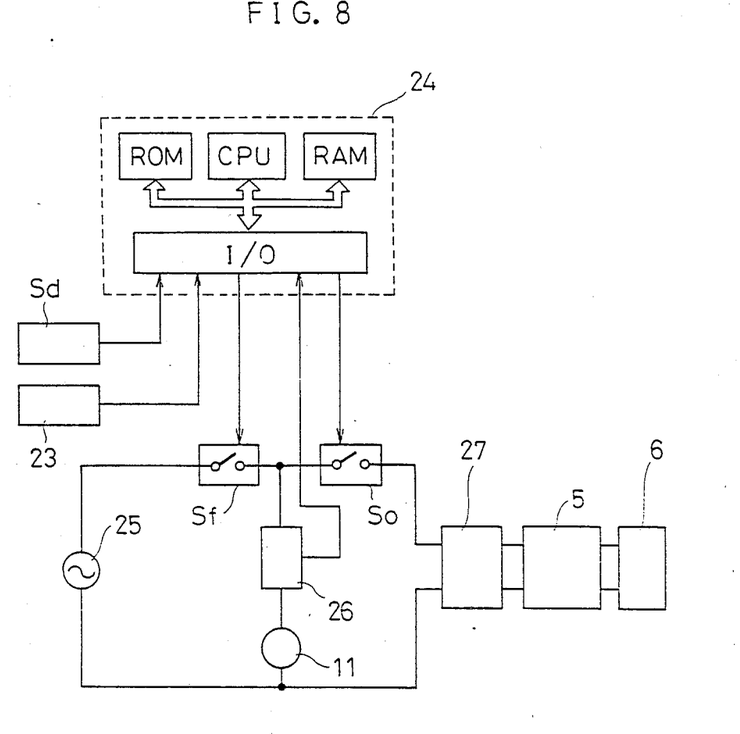
FIG. 8 is a block diagram showing a control circuit for the apparatus of FIGS. 6 and 7.

FIG. 8 is a fragmentary block diagram showing a control circuit for controlling the deodorizing apparatus of FIG. 6 and FIG. 7. The control circuit includes a microcomputer 24 having a ROM, a RAM a CPU and I/O ports, a 100 V a.c. power supply 25, switching elements Sf, So, such as triacs or relay contacts, a current detecting circuit 26 for detecting the presence or absence of the current for driving the motor 11, and a constant-voltage circuit 27. The power supply 25 supplies power to the motor 11 via the switching element Sf and the current detecting circuit 26. Also, the power supply 25 supplies power to the high voltage generating unit 5 by way of the switching elements Sf, So and the constant-voltage circuit 27. The microcomputer 24 receives signals from the door switch Sd, the temperature sensor 23 and the current detecting circuit 26 for controlling the on-off operation of the switching elements Sf, So. The switching elements Sf and the microcomputer 24 function as first control means to operate the electric motor while switching element So and the microcomputer 24 function as second control means to operate the ozone generator.

Figure 9:
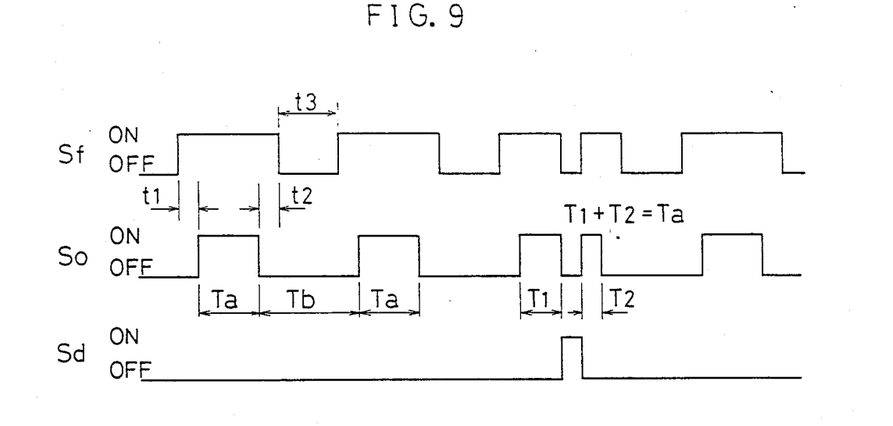
FIGS. 9 and 10 are time charts for illustrating the operation of the control circuit of FIG. 8.
Figure 10:
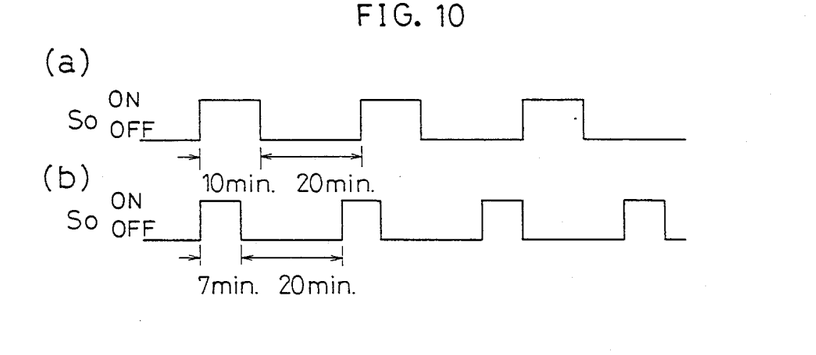

FIG. 9 is a time chart showing the operations of the switching elements Sf, So and the door switch Sd. FIG. 10 is a time chart showing a change in the on-period of the switching element So that is controlled according to the output of the temperature sensor 23.

With reference to these drawings, the operation of the deodorizing apparatus and the features of the operation will be described generally.

The microcomputer 24 includes timers (Ta timer and Tb timer), which function as a first timer to hold the switching element So on during a period of time Ta, and maintains the ozone generator 6 in operation during this period, (Ta mode) subsequently the switching element So is held off during a time interval Tb, and maintains maintaining the ozone generator 6 out of operation during this interval (Tb mode) as shown in FIG. 9. This cycle is repeated. According to the present embodiment, Ta is set to 10 minutes, and Tb is set to 20 minutes, in view of the capacity of the refrigerator 21 and the ability of the deodorizing catalyst 10. Thus, the ozone generator 6 is driven intermittently for 10 minutes at intervals of 20 minutes.

As previously stated, the ozone decomposition efficiency of the deodorizing catalyst 10 is not always 100% because the efficiency gradually decreases when the deodorizing catalyst 10 is in use for a long period of time, which permits the residual ozone to flow out from the air outlet 3 into the refrigerator, and results in an increased ozone concentration after the refrigerator which exceeds a given regulation value after several tens of years. According to the invention, however, the ozone generator 6 is driven intermittently at the above-mentioned interval for maintaining the interior ozone concentration below the regulation value at all times. Consequently, the interior ozone concentration will not exceed the regulation value of 0.1 ppm before 20 years, so that the deodorizing apparatus may operate with exceedingly high amount of safety.

The microcomputer 24 further incorporated a long-period timer therein which functions as a second timer (a 3-day timer for measuring the period of 3 days in the present embodiment), which forcibly turns off the ozone generator 6 and the motor 11 if the door 22 is held closed for more than a specified period of time, i.e. for more than 3 days, for preventing an increase in the interior ozone concentration. Furthermore, in response to a closing signal (Sd=OFF) from the door switch Sd, the microcomputer 24 energizes the motor 11 as will be described later and drives the ozone generator 6 for time periods Ta at intervals Tb as previously described above. If the door is opened during this mode of control, the motor 11 and the ozone generator 6 are deenergized in response to the door movement. The motor 11 and the generator 6 are thereafter energized in response to the closing of the door, whereupon the Ta or Tb timer resumes the time measuring operation for holding the ozone generator 6 in operation (or out of operation) during the remaining period of time.

Accordingly, the opening or closing of the door produces no variations in the on-period or the off-interval of the apparatus.

Furthermore, if the door is held closed for a long period of time, e.g., for days, the ozone generator 6 and the motor 11 are forcibly deenergized for preventing the interior ozone concentration from increasing.

The ozone generator has caused by the temperature and humidity around the discharge electrodes which affects the silent discharge and develops variations in the amount of ozone produced. Additionally, odors are perceived strongly at high temperatures but less strongly at low temperatures therefore, there is a need to control the deodorizing apparatus according to the temperature.

The present embodiment is therefore adapted to control the amount of ozone to be produced according to the internal temperature of the refrigerator detected by the temperature sensor 23. More specifically, the apparatus is driven intermittently for a cycle wherein the switching element So is on (for the production of ozone) for 10 minutes and off for 20 minutes as shown in FIG. 10 (a) when the internal temperature Th is greater than a set temperature Ts (5° C.) whereas, if the temperature Th becomes lower than the set temperature Ts, the cycle is changed so that the switching element So is on for 7 minutes and off for 20 minutes as seen in FIG. 10 (b) for decreasing the amount of ozone to be produced. Moreover, a plurality of temperature settings may be provided to give a more minutely altered time ratio for the intermittent operation to control the amount of ozone relative to the internal temperature Th. If the intermittent operation time ratio is adjusted similarly using a humidity sensor instead of the temperature sensor 23, a decrease in the amount of ozone due to an increase in humidity can be compensated.

Next, a description will be given for the operation of the motor 11 which drives the fan 12. As previously described, the motor 11 is controlled by the switching element Sf, which is turned on and off by signals from the microcomputer 24. As shown in FIG. 9, the ON signal for the switching element Sf is given earlier than the ON signal for the switching element So for operating the high voltage generating unit 5 by a period of time t1. The OFF signal for the switching element Sf is produced for a period of time t2 after an OFF signal is given to the switching element So.

Thus, when the high voltage generating unit 5 operates, the motor 11 is first operated, and the operation of the unit 5 is initiated for the period of time t1 thereafter. Furthermore, when the specified time t2 elapses after the unit 5 is brought out of operation, the motor 11 is deenergized. This mode of control causes the residual ozone to flow in the forward direction, preventing the ozone from flowing out from the case 1a in a reverse direction through the air inlet 2 which is especially applicable for the case of the deodorizing apparatus, as shown in FIG. 7. Although the motor 11 may be operated continuously and independently from the intermittent operation of the ozone generator 6, the motor 11 is driven intermittently as described above. Thereby, the motor 11 will operate for a prolonged period of time and the amount of power consumed will be reduced.

In the deodorizing apparatus of FIG. 6, the residual ozone is converted into oxygen by the deodorizing catalyst 4, and the motor 11 may be operated intermittently at the same interval as the ozone generator 6.

Figure 11:
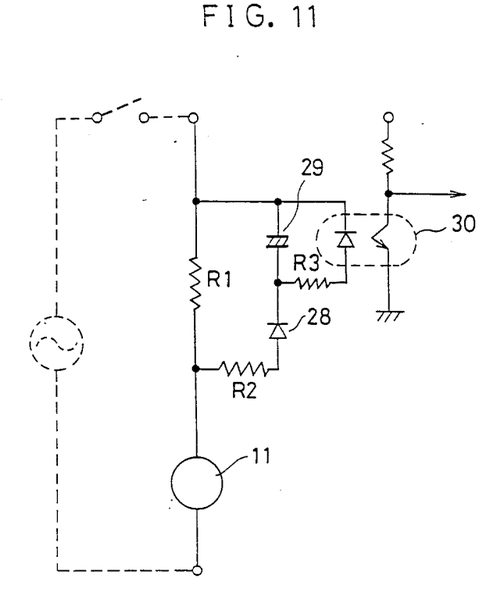
FIGS. 11 and 12 are fragmentary diagrams showing the circuit of FIG. 8 in greater detail.

Next, with reference to FIG. 11, the current detecting circuit 26 includes a resistor R1 connected in series with the motor 11, a series circuit having a resistor R2 and connected in parallel with the resistor R1 a diode 28 and capacitor R2, diode 28 and capacitor 29, and a series circuit having a resistor R3 and a photocoupler 300 and connected to both ends of the capacitor 29. While the motor 11 is in a normal operation, the resistor R1 produces a very low amount of a.c. voltage, which is converted to a d.c. voltage by the diode 28 and the capacitor 29. Consequently, the light-emitting diode in the photocoupler 30 is turned on, and the phototransistor therein is also brought into conduction, which indicates to the microcomputer 24 that the motor 11 is in normal operation. If a break occurs in the motor 11, on the other hand, current does not flow through the resistor R1 and voltage is not produced to the capacitor 29 which consequently turns off the lightemitting diode within the photocoupler 30. This indicates that the motor 11 is out of operation.

When a break in the motor 11 is detected, the high voltage generating unit 5 is deenergized, which causes the ozone generator 6 to discontinue the production of ozone. More specifically, if a break occurs in the motor 11 to stop the fan 12 for one reason or another during the operation of the deodorizing apparatus, the current detecting circuit 26 detects this break for the above described reason above, and the microcomputer 24 deenergize to the high voltage generating unit 5. Consequently, the ozone generator 6 does not produce ozone and the outflow of ozone is precluded due to the stopping of the motor 11.

The switching elements Sf and So are connected into the control circuit as will be described below. The switching element Sf is connected in series with a parallel circuit which includes the motor 11 and the series circuit of the high voltage generating unit 5 and the switching element So.

Accordingly, when an ON signal is intermittently emitted by the microcomputer 24, the switching elements Sf and So are closed for energizing the high voltage generating unit 5 and the motor 11.

Suppose the switching element So is held turned on at all times due to a malfunction. Even then, the high voltage generating unit 5 is not energized, and the ozone generator 6 does not produce ozone unless the switching element Sf is turned on, i.e. unless the motor 11 is driven. Incidentally, if ozone is produced while the motor 11 is stopped, ozone will flow into the refrigerator which creates a great hazard especially in the case of the embodiments shown by FIGS. 2 and 7.

Furthermore, if the switching element Sf malfunctions and does not close for one reason or another, the high voltage generating unit 5 similarly does not energize, and the ozone generator 6 does not produce ozone.

The construction described above obviates the continuous production of ozone due, for example, to the malfunction or failure of the switching elements Sf and So, and assures that the deodorizing apparatus will operate at a high degree of safety.

Figure 12:
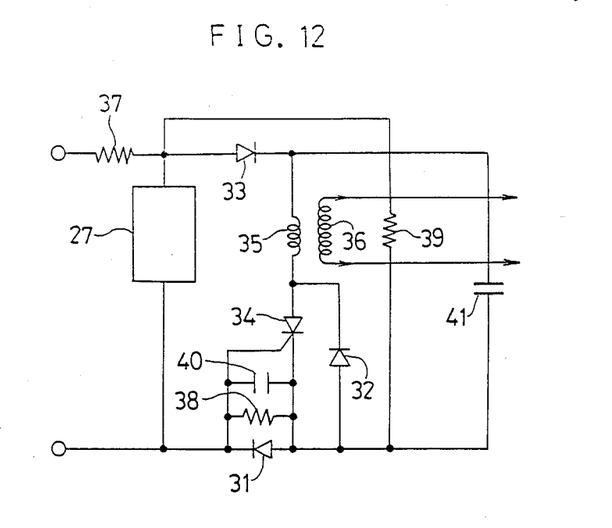

The high voltage generating unit 5 and the constant-voltage circuit 27 will be described next with reference to FIGS. 12 and 13. FIG. 12 shows diodes 31, 32 and 33, a thyristor 34 connected in series with a primary winding 35, a secondary winding 36 connected to the ozone generator 6, resistors 37, 38, and 39, and capacitors 40 and 41. A high voltage is applied to the ozone generator 6 by the charging and discharging of the capacitor 41 and the conduction and nonconduction of the thyristor 34.

The amount of ozone to be produced by the generator 6 varies with the voltage applied from the high voltage generating unit 5. Therefore, the amount of ozone must be made constant by applying a constant voltage to the generator 6. More specifically stated with reference to FIG. 13, curve (A), the amount of ozone to be produced varies with the primary voltage of the unit 5. Therefore, the primary voltage of the unit 5 must be constant.

Figure 13:
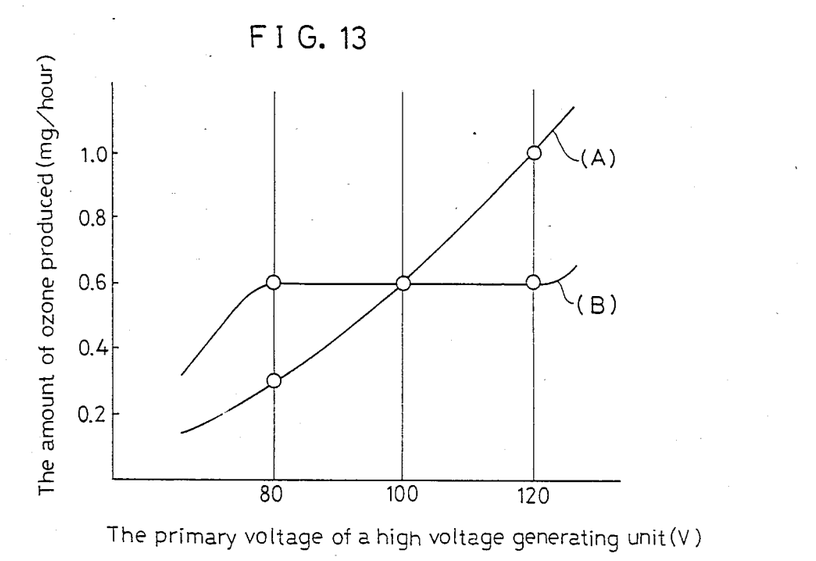
FIG. 13 is a graph comparing the relation between the amount of ozone produced and the primary voltage of a high voltage generating unit as established by the deodorizing apparatus of the invention and the conventional apparatus.

The constant-voltage circuit 27 provided for the high voltage generating unit 5 according to the invention makes it possible to apply a constant voltage to the ozone generator 6, which enables the generator to produce ozone in a constant amount as shown in FIG. 13, curve (B), and assures the apparatus of a stabilized deodorizing operation.

The term "constant voltage" refers to the secondary voltage of the unit 5. The secondary voltage variations are ±5% relative to a standard value even if the primary voltage of the unit varies in the range of 80 to 120 V.

Figure 14:
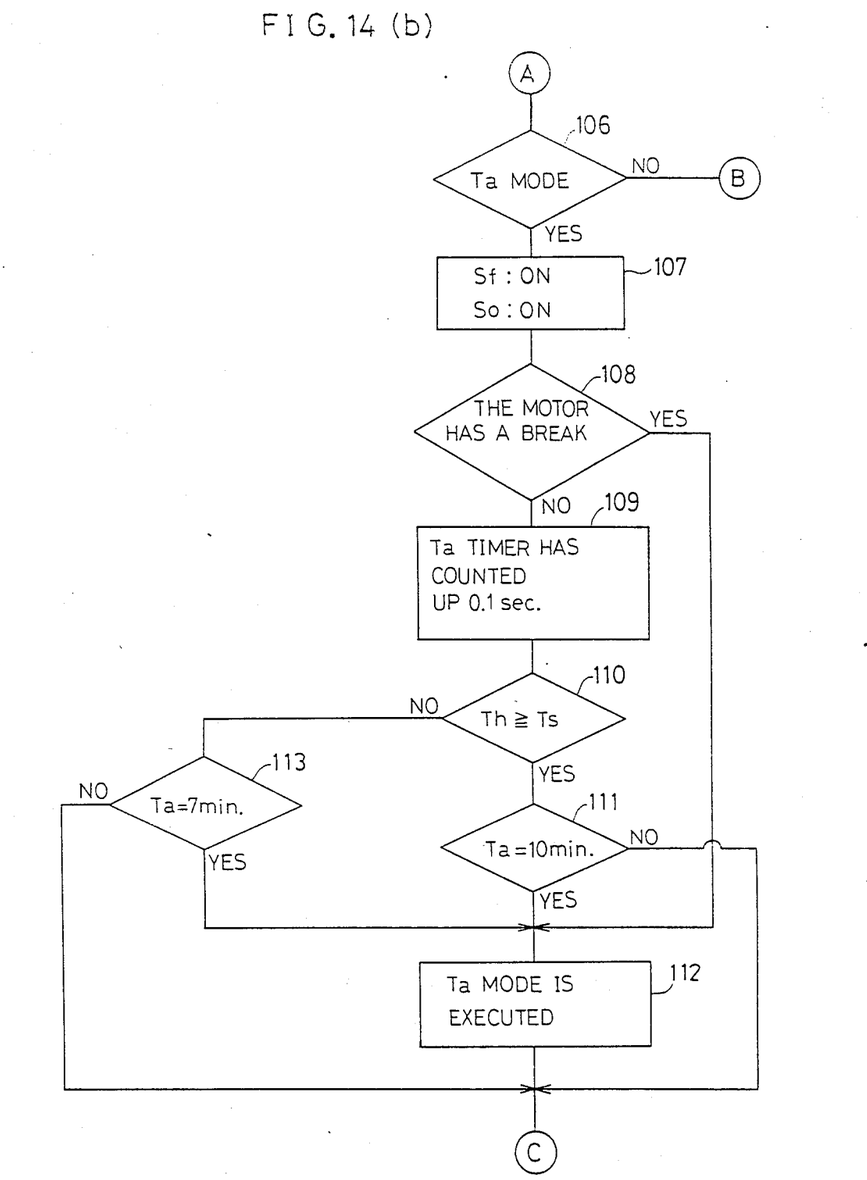
Figure 14A:
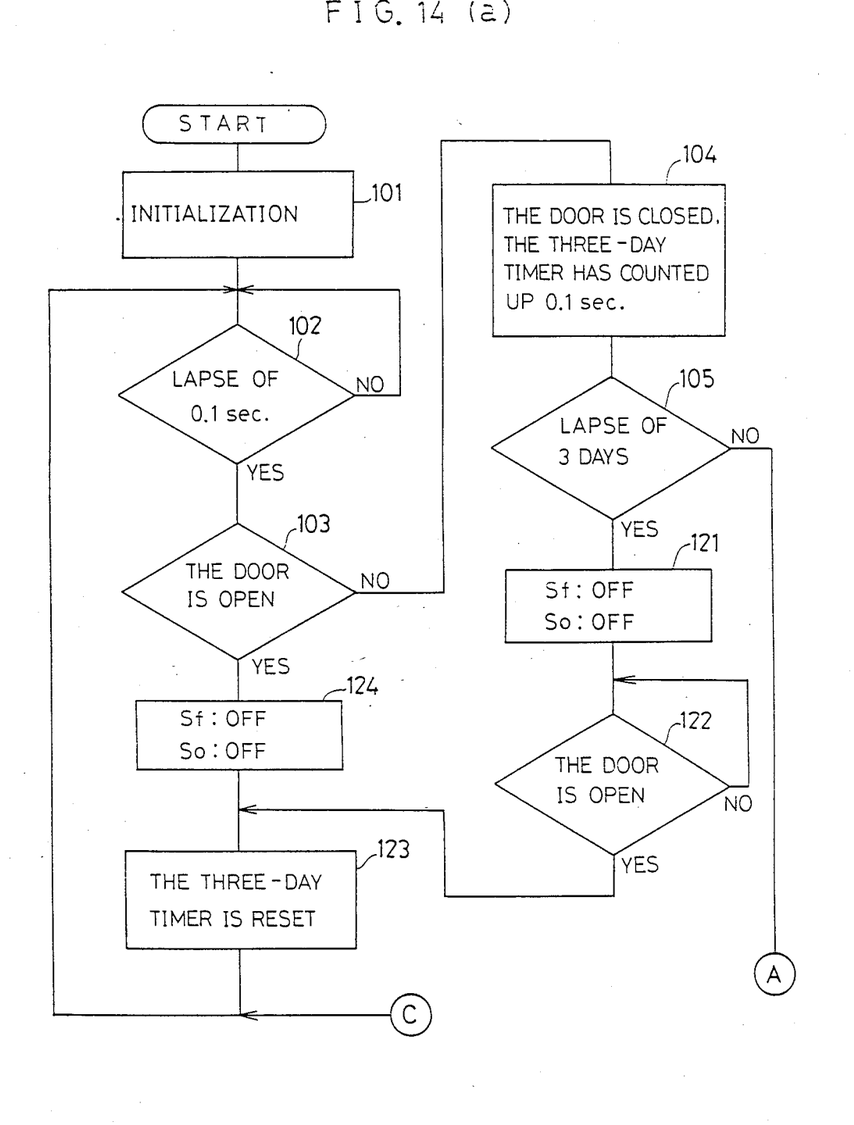

The operation of the deodorizing apparatus will be described collectively with reference to the flow charts of FIG. 14 (a) to FIG. 14 (c). When the operation of the apparatus is initiated, the control system is initialized (step 101). The sequence shown in the flow charts proceeds from step to step at intervals of 0.1 second as measured by an internal timer of the microcomputer 24, so that upon a lapse of 0.1 second (step 102), the door 22 is checked. If the door is found closed with the door switch Sd off, the three-day timer is started (steps 103 and 104). While the three-day timer is in a counting operation (step 105), the Ta mode follows (step 106), in which both the switching elements Sf and So are turned on (step 107). Unless the motor 11 has a break, the Ta timer is started (step 109). When the temperature Th detected by the temperature sensor 23 is greater than the set temperature Ts (5° C.) (step 110) and upon a lapse of 10 minutes, i.e. the time Ta (step 111), Tb mode is executed (step 112). If Th is lower than Ts in step 110 and the time Ta of 7 minutes (step 113) elapses, the tb mode is executed. In the Tb mode, when the time Tb measured by the Tb timer reaches t1 (step 114), only the switching element Sf is turned on. If t1<Tb<t2+t3, both the switching elements Sf and So are turned off, or if Tb≧t2+t3, only the switching element Sf is turned on (step 116 or 117). Upon the Tb timer counting up to the time Tb (20 minutes) (steps 118 and 119), the Ta mode follows again (step 120). When the door 22 has been held closed for three days (step 105), both the switching elements Sf and So are turned off (step 121). When the door 22 is subsequently opened (step 122), the three-day timer is reset (step 123). If the door 22 is opened in the Ta or Tb mode (step 103), both the switching elements Sf and So are turned off, and the three-day timer is reset (steps 124 and 123).

The deodorizing apparatus according to the present invention can be conveniently installed in refrigerators as explained above and also in other closed chambers such as cabins of automobiles.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A deodorizing apparatus comprising:
   a case having an air flow channel provided therein having an air inlet disposed at a first end of said air flow channel and an air outlet disposed at a second end of said air flow channel opposite to said first end;
   an ozone generator disposed in said air flow channel between said air inlet and said air outlet, said ozone generator being of a discharge type;
   first acceleration means disposed in said air flow channel adjacent to said air outlet for accelerating the decomposition of odors and ozone;
   a fan disposed within said case;
   an electric motor disposed with said case for driving said fan; and
   second acceleration means disposed in said air flow channel adjacent to said air inlet for preventing an excess of ozone from flowing out by accelerating the decomposition of odors and ozone.

2. An apparatus as defined in claim 1, wherein said air inlet, said second acceleration means, said ozone generator, said first acceleration means, said electric motor, said fan and said air outlet are arranged in this order.

3. An apparatus as defined in claim 1, wherein said ozone generator comprises a high voltage generating circuit having a constant-voltage circuit at a power supply input side, thereof.

4. An apparatus as defined in claim 1, wherein said first acceleration means comprises a plate having a honeycomb structure, said plate comprising a material capable of accelerating the decomposition of odors and ozone.

5. An apparatus as defined in claim 1, wherein said air inlet, said electric motor, said second acceleration means, said fan and said air outlet are arranged in this order in said air flow channel.

6. An apparatus as defined in claim 1, wherein said electric motor and said ozone generator are driven by an output voltage of a step-down transformer connected to a commercial power supply.

7. An apparatus as defined in claim 6, wherein the step-down transformer is housed in a transformer case separate from said case of the deodorizing apparatus.

8. An apparatus as defined in claim 7, wherein said case of the deodorizing apparatus is connected to said transformer case by a two-core cable.

9. An apparatus as defined in claim 8 wherein said two-core cable is removably connected to said transformer case.

10. An apparatus as defined in claim 7, wherein said transformer case comprises blades capable of being inserted into a commercial power supply receptacle for removably connecting said transformer case to said commercial power supply receptacle.

11. An apparatus as defined in claim 1, wherein the deodorizing apparatus is installed within a refrigerator having a door.

12. An apparatus as defined in claim 11, further comprising first control means for controlling the operation of said electric motor, and second control means for intermittently operating said ozone generator at predetermined ON- and OFF-periods.

13. An apparatus as defined in claim 12, wherein said first control means intermittently operates said electric motor in an operative relation to the intermittent operation of said ozone generator by said second control means.

14. An apparatus as defined in claim 12, wherein said first control means operates said electric motor for a period of time greater than said predetermined ON-period of said ozone generator.

15. An apparatus as defined in claim 12, wherein said electric motor comprises current detecting means in a drive current circuit of said electric motor.

16. An apparatus as defined in claim 15, wherein said current detecting means detects the absence of a drive current for said electric motor and prevents said second control means from operating said ozone generator in response to the absence of said drive current.

17. An apparatus as defined in claim 11, wherein said case comprises a portion of the inner wall of said refrigerator.

18. An apparatus as defined in claim 12, wherein a common a.c. power supply supplies drive power to said electric motor and said ozone generator.

19. An apparatus as defined in claim 18, wherein said first control means comprises first switching means for opening and closing a first circuit for supplying said drive power from said common a.c. power supply to said electric motor and said ozone generator, and said second control means comprises second switching means for opening and closing a second circuit for supplying power from said switching means to said ozone generator.

20. An apparatus as defined in claim 12, wherein said first and second control means comprises a microcomputer.

21. An apparatus as defined in claim 12, wherein said refrigerator includes a temperature sensor and a humidity sensor in the interior of said refrigerator.

22. An apparatus as defined in claim 21, wherein said second control means is responsive to an output from said temperature sensor and said humidity sensor for intermittently operating said ozone generator by controlling said predetermined ON- and OFF-periods.

23. An apparatus as defined in claim 12, wherein said refrigerator includes a door switch operative in response to the opening and closing of said door.

24. An apparatus as defined in claim 23, wherein said second control means comprises a first timer for measuring and setting said predetermined ON-period of the intermittent operation of said ozone generator, said second control means interrupts the measuring operation of said first timer and the intermittent operation of said ozone generator, and causes said first timer and said ozone generator to resume operating.

25. An apparatus as defined in claim 24, wherein said second control means comprises a second timer for measuring a closed period of time during which said door is closed, and prevents the operation of said ozone generator when the door is closed for at least a predetermined period of time.

26. An apparatus as defined in claim 11, wherein said ozone generator comprises a high voltage generating circuit having a constant-voltage circuit at a power supply input side, thereof.

27. An apparatus as defined in claim 23, wherein said second control means comprises a second timer for measuring a closed period of time during which said door is closed and prevents the operation of said ozone generator when the door is closed for at least a predetermined period of time.

28. A deodorizing apparatus comprising:
a case having an air flow channel therein with an air inlet disposed at a first end of said air flow channel and an air outlet disposed at a second end of said air flow channel opposite to said first end;
an ozone generator disposed in said air flow channel between said air inlet and said air outlet, said ozone generator being of a discharge type;
first acceleration means disposed in said air flow channel adjacent to said air outlet for accelerating the decomposition of odors and ozone;
a fan disposed within said case; and
an electric motor disposed in said air flow channel adjacent to said air inlet for driving said fan and preventing an excess of ozone from flowing out.

29. An apparatus as defined in claim 26, wherein said air flow channel is U-shaped, and said air inlet, said electric motor, said ozone generator, said first acceleration means, said fan and said air outlet are arranged in this order.

30. An apparatus as defined in claim 28, wherein said air inlet, said electric motor, said fan, said ozone generator, said first acceleration means and said air outlet are arranged in this order from said first end of the deodorizing apparatus upward against the direction of gravity.

* * * * *